United States Patent [19]

Michaelson et al.

[11] Patent Number: 4,533,773

[45] Date of Patent: Aug. 6, 1985

[54] PROCESS FOR HYDROXYLATING OLEFINS IN THE PRESENCE OF AN OSMIUM OXIDE CATALYST AND CARBOXYLATE SALT CO-CATALYST

[75] Inventors: Robert C. Michaelson, Waldwick; Richard G. Austin, Ridgewood, both of N.J.

[73] Assignee: Exxon Research & Engineering Co., Florham Park, N.J.

[21] Appl. No.: 592,284

[22] Filed: Mar. 22, 1984

Related U.S. Application Data

[63] Continuation-in-part of Ser. No. 394,414, Jul. 1, 1982, abandoned.

[51] Int. Cl.³ ............... C07C 29/04; C07C 31/18; C07C 31/22; C07C 31/42
[52] U.S. Cl. ................... 568/860; 560/186; 562/587; 568/811; 568/821; 568/833; 568/838; 568/847; 260/397.2
[58] Field of Search ............... 568/860, 833, 811, 821, 568/838, 847; 562/587; 560/186; 260/397.2

[56] References Cited

U.S. PATENT DOCUMENTS

| | | | |
|---|---|---|---|
| 2,773,101 | 12/1956 | Smith et al. | 568/860 |
| 2,813,130 | 11/1957 | Keeler et al. | 568/860 |
| 3,317,592 | 5/1967 | MacLean et al. | 568/860 |
| 3,931,342 | 1/1976 | Sheng | 568/860 |
| 4,049,724 | 9/1977 | Sheng et al. | 568/860 |
| 4,255,596 | 3/1981 | Wu et al. | 568/860 |

*Primary Examiner*—J. E. Evans
*Attorney, Agent, or Firm*—Robert A. Maggio

[57] ABSTRACT

A process for hydroxylating olefins, such as ethylene or propylene, using an osmium oxide catalyst such as $OsO_4$, a carboxylate salt co-catalyst, such as sodium acetate, and organic hydroperoxide oxidant is disclosed.

10 Claims, No Drawings

PROCESS FOR HYDROXYLATING OLEFINS IN THE PRESENCE OF AN OSMIUM OXIDE CATALYST AND CARBOXYLATE SALT CO-CATALYST

CROSS-REFERENCE TO RELATED APPLICATION

This application is a continuation-in-part of U.S. patent application Ser. No. 394,414, filed July 1, 1982, now abandoned.

BACKGROUND OF THE INVENTION

This invention relates to the hydroxylation of olefins. In particular, it relates to a procedure for reacting an olefin, e.g. ethylene or propylene, with an organic hydroperoxide oxidant in the presence of a specific catalyst composition and solvent to produce the corresponding glycol.

It is well known from the technical literature, including patents, that olefins can be effectively oxidized with osmium oxide compounds, particularly osmium tetroxide, to their corresponding diols when the reaction is carried out with organohydroperoxide oxidants and catalytic amounts of osmium tetroxide. However, because of the low activity and/or selectivity of $OsO_4$ as a catalyst when employed alone, various promoters or co-catalysts have been employed in conjunction with $OsO_4$ to enhance the rate and/or selectivity of the hydroxylation reaction.

More specifically, Japanese Patent Application No. Sho 54-145604, published Nov. 14, 1979, is directed to a process for hydroxylating olefins in the presence of $OsO_4$, a quaternary ammonium salt co-catalyst such as tetra ethyl ammonium bromide, and a peroxide including organo peroxides and $H_2O_2$ as the oxidant. Selectivities to glycol of from about 4.5 to about 66% are disclosed. It is to be noted, however, that the critical component of the co-catalyst as implied in this patent is the quaternary ammonium cation rather than the particular identity of the anion, since the anion can be any of halogen, hydroxy, nitrate, perchlorate, sulfate, methane sulfonate, trifluoromethane sulfonate, and tetra fluoro borate ions, while the cation must always be quaternary ammonium. Carboxylate anions are not disclosed in this application.

K. B. Sharpless et al, teach in a recent publication J. Org. Chem, Vol. 43 p. 2063 (1978), that tetra alkyl ammonium acetate can be used advantageously as a cocatalyst for the hydroxylation of olefins to corresponding vicinal diols using $OsO_4$ as a catalyst, and alkyl hydroperoxides as oxidants, provided that the solvent employed is acetone instead of t-butanol, a conventional solvent or co-solvent for such type of reactions. In addition, Sharpless et al disclose the use of excessive amounts of the expensive tetra alkyl ammonium carboxylate salt. The Sharpless et al system from a commercial standpoint is disadvantageous in that the required use of acetone as a solvent complicates the separation of the glycol product, and alcohol by-product derived from the organohydroperoxide oxidant, from the reaction mixture and necessitates the use of additional and expensive distillation equipment required for recycle of the acetone back to the hydroxylation reactor.

The search has therefore continued for co-catalysts which can be employed in conjunction with $OsO_4$.

Accordingly, it would be of extreme economic significance if co-catalysts could be identified which do not possess the drawbacks of those of the prior art. Commercial olefin hydroxylation systems should be capable of employing as solvents materials which are formed during the hydroxylation reaction and/or materials which are present in commercially available organic hydroperoxides.

For example, during the hydroxylation reaction the organic hydroperoxide, such as t-butyl hydroperoxide (TBHP) will form its corresponding alcohol, such as t-butylalcohol (TBA), as follows, using TBHP as the oxidant, and propylene as the olefin to be hydroxylated:

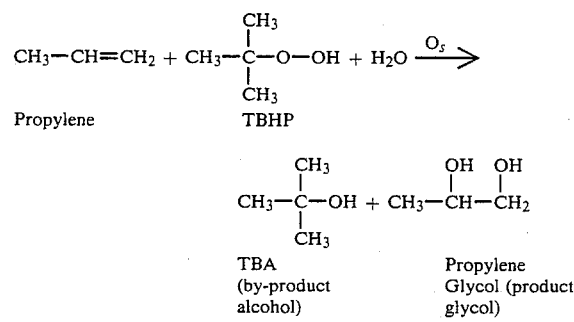

Moreover, commercially available organic hydroperoxides such as TBHP are sold as mixtures of the peroxide and the by-product alcohol TBA. Consequently, a commercial hydroxylation system should not require separation of the by-product alcohol from the reaction mixture before recycle or purification of the commercially available organic hydroperoxide before use.

The search has therefore continued for co-catalysts which can be employed in conjunction with $OsO_4$ catalyst and organohydroperoxide oxidant to increase the rate and/or selectivity of the hydroxylation reaction in a commercially suitable manner.

The present invention is a result of this search.

Commonly assigned U.S. Pat. No. 4,413,151 by Michaelson, Austin and White, discloses a supported osmium catalyst which can be employed in conjunction with various co-catalysts including carboxylate salts. The description of these salts and their use as co-catalysts in conjunction with $OsO_4$ is based on the details of the process of the present invention.

While none of the prior art of which applicants are aware disclose the use of carboxylate salts as cocatalysts for use with a $H_2O_2$ oxidant in accordance with the present invention, the following patents are discussed to provide a general background of the prior art employing osmium catalysts.

U.S. Pat. No. 2,414,385 discloses the use of hydrogen peroxide and a catalytically active oxide, such as osmium tetroxide, dissolved in an essentially anhydrous non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° C. and 21° C. Such low reaction temperatures drastically, and disadvantageously, reduce the reaction rate to commercially unacceptable levels. At temperatures greater than 21° C., the formation of aldehydes, ketones and acids is favored.

U.S. Pat. No. 2,773,101 discloses a method for recovering an osmium containing catalyst such as tetroxide, by converting it to the non-volatile osmium dioxide form, distilling the hydroxylation product, reoxidizing the osmium dioxide to the volatile osmium tetroxide, and then recovering the same by distillation. Suitable oxidizing agents used to oxidize olefins, and re-oxidize the osmium dioxide, include inorganic peroxides such as hydrogen peroxide, sodium peroxide, barium peroxide; organic peroxides, such as t-butyl peroxide or hydroperoxide, benzoyl peroxide; as well as other oxidizing agents such as oxygen, perchlorates, nitric acid, chlorine water and the like. As with other methods of the prior art, the above process yields undesirable by-products (see col. 1, line 55) thus reducing the selectivity of the process.

British Patent Specification No. 1,028,940 is directed to a process for regenerating osmium tetroxide from reduced osmium tetroxide by treatment of the latter with molecular oxygen in an aqueous alkaline solution. More specifically, it is disclosed that when osmium tetroxide is used by itself as an oxidizing agent, or as a catalyst in conjunction with other oxidizing agents, to oxidize hydrocarbons, the osmium tetroxide becomes reduced, and in its reduced form is less active than osmium tetroxide itself. Consequently, by conducting the oxidation reaction in the presence of an alkaline medium and supplying oxygen to the medium throughout the process, the osmium tetroxide is maintained in a high state of activity. The oxidation products disclosed include not only ethylene glycol from ethylene but also organic acids from such compounds as vicinal glycols, olefins, ketones and alcohols.

U.S. Pat. No. 4,255,596 is directed to a process for preparing ethylene glycol in a homogeneous single-phase reaction medium using ethylbenzene hydroperoxide as the oxidizing agent dissolved in ethylbenzene and osmium tetroxide as the catalyst. The pH of the reaction medium is maintained at about 14 by the presence of tetraalkyl ammonium hydroxide. A small amount of water can dissolve beneficially in the medium to reduce by-product formation and improve selectivity to the glycol.

U.S. Pat. No. 4,049,724 describes the preparation of glycols from alkenes and from unsaturated alcohols in an aqueous system using osmium tetroxide and specifying stable and water-soluble aliphatic hydroperoxides, such as t-butyl hydroperoxide, while a critical pH of 8 to 12 is maintained by a suitable combination of alkali metal buffering compounds. The preparation of propylene glycol utilizing t-butyl hydroperoxide is exemplified in the patent at a selectivity based on the hydroperoxide of 45%.

U.S. Pat. No. 3,335,174 is directed to the use of water hydrolyzable Group Vb, VI-b and VII metal halides and oxyhalides (e.g., $OsCl_3$) as hydroxylation and esterification catalysts in conjunction with aqueous $H_2O_2$ as an oxidant. However, the process for using this catalyst requires the presence of lower aliphatic hydrocarbon acids such as glacial, formic, acetic and propionic acid as solvents. Under these conditions the reaction times vary from ½ to 4 hours, but at the shorter reaction times it is disclosed that substantial amounts of epoxide result. The only yield disclosed is obtained in connection with tungsten hexachloride in Example 1. This yield is extremely low, i.e., 22%, and includes both half-acetate and diol. Thus, among the major disadvantages of the process described in this patent are the low selectivities to diol and the corrosiveness of metal halides in the presence of glacial acids such as acetic acid.

See also: U.S. Pat. No. 3,317,592 (discloses production of acids and glycols using oxygen as oxidant, $OsO_4$ as catalyst at pH 8 to 10); U.S. Pat. No. 3,488,394 (discloses hydroxylation of olefins by reacting olefin and hypochlorite in the presence of $OsO_4$); U.S. Pat. No. 3,846,478 (discloses reaction of hypochlorite and olefin in an aqueous medium and in the presence of $OsO_4$ catalyst to hydroxylate the olefin); U.S. Pat. No. 3,928,473 (discloses hydroxylation of olefins to glycols with $O_2$ oxidant, octavalent osmium catalyst (e.g. $OsO_4$), and borates as promoter); U.S. Pat. No. 3,391,342 (discloses a process for recovering glycols from an aqueous solution containing alkali metal borate and osmium compounds (e.g. $OsO_4$); U.S. Pat. No. 3,953,305 (discloses use of $OsO_4$ catalyst for hydroxylating olefins which is regenerated by oxidizing hexavalent osmium with hexavalent chromium and electro-chemically regenerating hexavalent chromium); U.S. Pat. No. 4,203,926 (discloses ethylbenzene hydroperoxide as oxidant used in two-phase system to hydroxylate olefins in presence of $OsO_4$ and cesium, rubidium and potassium hydroxides); U.S. Pat. No. 4,217,291 (discloses the oxidation of Osmium (III) or (IV) in an ionic complex with oxygen and an alkali metal, ammonium, or tetra (-lower) alkyl ammonium cation to a valency of greater than +5+organohydroperoxides); U.S. Pat. No. 4,229,601 (discloses the use of cesium, rubidium and potassium hydroxides as promoters for $OsO_4$ catalyst and t-butyl hydroperoxide oxidant for hydroxylating olefins); and U.S. Pat. No. 4,280,924 (discloses a process for regenerating perosmate catalyst, e.g., cesium, rubidium and potassium perosmate).

SUMMARY OF THE INVENTION

In one aspect of the present invention there is provided a process for hydroxylating olefins which comprises reacting at least one olefinic compound having at least one ethylenic unsaturation, with at least one organic hydroperoxide and water in the presence of a catalyst composition under conditions and in a manner sufficient to convert at least one of said ethylenic unsaturation to its corresponding vicinal diol said catalyst composition comprising: (a) at least one osmium oxide capable of catalyzing said hydroxylation reaction; and (b) as a co-catalyst at least one organic carboxylate salt having a cation and a anion, said cation being selected from cations of alkali metal, alkaline earth metal, and transition metal said transition metal being selected from Fe, Co, Ni, Cu, V, Cr, Mn, Sc, Ti, Ru, Rh, Pd, and W; said co-catalyst being capable of increasing at least one of the rate and selectivity of the hydroxylation reaction to product diol relative to the rate and selectivity in the absence of said co-catalyst.

In another aspect of the present invention there is provided a process for hydroxylating olefins which comprises contacting in liquid admixture:
(a) at least one olefin having at least one ethylenic unsaturation;
(b) at least one organic hydroperoxide;
(c) water;
(d) at least one organic solvent; and
(e) a catalyst composition comprising:
   (i) at least one osmium oxide capable of catalyzing the hydroxylation reaction; and (ii) as a co-catalyst at least one carboxylate salt capable of increasing at least one of the rate and selectivity of the hydroxylation reaction to the hydroxylated product relative to the absence of said co-catalyst.

The contacting is conducted in a manner and under conditions sufficient to convert at least one of said olefin ethylenic unsaturation to its corresponding vicinal diol hydroxylated product and thereby also forming a by-product alcohol derived from the organic hydroperoxide. The organic solvent comprises at least 50%, by solvent weight, of a member selected from the group consisting of hydroxylated product, by-product alcohol, and mixtures thereof.

DESCRIPTION OF PREFERRED EMBODIMENTS

In accordance with the present invention, at least one olefin containing at least one ethylenic unsaturation is reacted with at least one organic hydroperoxide and water in the presence of a catalyst composition comprising at least one osmium oxide catalyst, and at least one organic carboxylate salt and optionally at least one specifically defined solvent under conditions and in a manner sufficient to hydroxylate at least one of said ethylenically unsaturated groups to its corresponding vicinal diol group.

1. Catalyst Composition (a) Osmium oxide catalyst

The preferred osmium oxide catalyst which is employed in unsupported form in the process of the present invention is osmium tetroxide, i.e. $OsO_4$.

However, included within the term osmium oxide as used herein are osmium compounds which are or can be converted to osmium tetroxide during the course of reaction such as salts thereof including K, Na, and Li, osmates and perosmates as well as other osmium oxides such as $OsO_2$, $OsO_3$, and the like.

(b) Co-catalyst

The co-catalyst which is employed in conjunction with the osmium oxide catalyst comprises at least one organic carboxylate salt, e.g., having an anion and a cation. The co-catalyst increases the rate and/or selectivity of the hydroxylation reaction.

More specifically, the hydrocarbyl portion of the anion of the carboxylate salt can be saturated aliphatic, saturated alicyclic, and aromatic. Moreover, it is the carboxylate —COO⁻) functional group which is believed to be responsible for the co-catalytic activity of the salt.

Accordingly, the anion of the carboxylate salt can be represented by the structural formula:

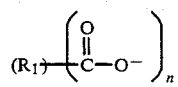  (I)

wherein $R_1$ represents a substituted or unsubstituted hydrocarbyl group selected from saturated aliphatic, typically saturated aliphatic having from about 1 to about 10, preferably from about 1 to about 5, and most preferably from about 1 to about 3 carbons exclusive of substituents; saturated alicyclic, typically saturated alicyclic having from about 4 to about 12, preferably from about 5 to about 10, most preferably from about 6 to about 8 carbons exclusive of substituents; and aromatic, typically aromatic having from about 6 to about 14, preferably from about 6 to about 10, most preferably 6 carbons exclusive of substituents; said $R_1$ substituents independently including, alkyl, typically alkyl of from about 1 to about 10, preferably from about 1 to about 5, most preferably from about 1 to about 3 carbons, aryl, typically aryl of from about 6 to about 14, preferably from about 6 to 10, most preferably 6 carbons, hydroxy, an ether group represented by the structural formulae —O—$R_2$ and —$R_3$—O—$R_2$ wherein $R_2$ and $R_3$ are independently selected from the group consisting of alkyl, typically about $C_1$ to about $C_{10}$ alkyl, preferably about $C_1$ to about $C_5$ alkyl, and most preferably about $C_1$ to about $C_3$ alkyl; and an ester group represented by the structural formulae:

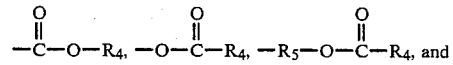

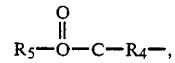

wherein $R_4$ and $R_5$ which may be the same or different are as defined in connection with $R_2$ and $R_3$; and mixtures thereof; and n in structural formula I is a number of from 1 to about 10, preferably from 1 to about 5, and most preferably from 1 to about 2 (e.g. 1).

The cation of the carboxylate salt typically is selected from cations of alkali metals (e.g. Li, Na, K, Rb, Cs, and Fr); alkaline earth metals (e.g. Be, Mg, Ca, Sr, Ba, Ra); tetrahydrocarbyl ammonium; tetrahydrocarbyl phosphonium; transition metals including those selected from the group consisting of Fe, Co, Ni, Cu, V, Cr, Mn, Sc, Ti, Mo, Ru, Rh, Pd and W; preferably Cu, Fe, Ni, Co, Mn; most preferably Cu, and Fe; and mixtures thereof.

The tetra hydrocarbyl ammonium or phosphonium cations can be represented by the respective structural formula $(R)_4N^+$ and $(R)_4P^+$ wherein R is a hydrocarbyl group independently selected from the group consisting of substituted and unsubstituted: alkyl, typically alkyl having from about 1 to about 30 carbons, preferably from about 1 to about 20 carbons, and most preferably from about 1 to about 10 (e.g. 1–5) carbons, aryl, typically aryl having from 6 to about 14 carbons, preferably about 6 to about 10 carbons, and most preferably 6 carbons, and alkaryl and aralkyl wherein the aryl and alkyl groups thereof are as described immediately above; said R substituents being as defined in connection with the substituents of $R_1$ described above. Accordingly, the term hydrocarbyl is intended to include both substituted and unsubstituted groups, and mixtures thereof.

The preferred cations are those of the alkali and alkaline earth metals, the most preferred being the alkali metal cations, e.g. Na, and K, due to cost considerations.

The preferred anions of the carboxylate salts are those having saturated aliphatic or aromatic hydrocarbyl groups, most preferably saturated aliphatic.

Illustrative examples of carboxylate salt cocatalysts include: sodium acetate, potassium acetate, calcium acetate, cesium acetate, magnesium acetate, potassium ethanoate, sodium propanoate, magnesium butanoate, strontium pentanoate, sodium benzoate, potassium benzoate, magnesium benzoate, calcium benzoate, sodium naphthoate, potassium naphthoate, beryllium naphthoate, sodium 4-(6-methyl-2-naphthyl) pentanoate, potassium 3-(7-methyl-1-naphthyl)-propanoate, magnesium 2-(4-propyl-1-benzyl) ethanoate, sodium 3-(ethoxy) proponoate, potassium 4-(propoxy carbonyl) butanoate, calcium 3-(propyl carbonyl oxy) propanoate, magnesium 2-(methyl carbonyl oxy methyl) acetate, beryllium 4-(ethoxy carbonyl methyl) butanoate, cesium 4-(ethoxy methyl) benzoate, sodium 3-(propoxy) naphthoate, potassium 4-(ethoxy carbonyl) benzoate, barium 2-(hydroxy) acetate, rubidium propanoate, magnesium 4-bromobenzoate, tetraethyl ammonium acetate, tetra butyl phosphonium acetate, phenyl triethyl ammonium acetate, phenyl trimethyl phosphonium acetate, tetraethyl ammonium benzoate, phenyl trimethyl phosphonium benzoate, phenyl triethyl ammonium naphthoate, tetra 4-hydroxy butyl ammonium acetate, tetra 3-hydroxypropyl phosphonium acetate, copper acetate, copper benzoate, copper naphthoate, copper propanoate, iron acetate, iron benzoate, iron naphthoate, copper 4-ethyl benzoate, nickel benzoate, nickel acetate, nickel naphthoate, cobalt (II) acetate, cobalt (II) benzoate, vanadyl acetate, vanadyl naphthenate, chromium (III) acetate, molybdenyl (V) acetate, manganese (III) acetate, palladium (III) acetate, rhodium (III) acetate, tungstenyl (V) naphthenate, tungstenyl (V) acetate, and mixtures thereof.

Representative examples of multifunctional carboxylate containing co-catalysts include the Na, K, Rb, Cs, tetraethyl ammonium, and tetraethyl phosphonium: oxylates, malonates, succinates, adipates and the like.

Preferred co-catalysts include the Na, K, Rb and Cs acetates, tetra ethyl ammonium acetate, tetra ethyl phosphonium acetate, copper acetate, iron acetate and mixtures thereof.

The most preferred co-catalysts include the Na, K, Rb and Cs acetates.

The osmium containing catalysts are employed in amounts effective to catalyze the hydroxylation reaction. Thus, while any effective amount of osmium catalyst will suffice, it is contemplated that such effective amounts constitute typically from about $1 \times 10^{-1}$ to about $1 \times 10^{-8}$ moles, preferably from about $1 \times 10^{-2}$ to about $1 \times 10^{-6}$ moles, and most preferably from about $1 \times 10^{-2}$ to about $1 \times 10^{-5}$ moles, of osmium in the osmium catalyst per mole of olefin ethylenic unsaturation to be hydroxylated.

Alternatively, such amounts may be expressed as varying from about 1 to about 10,000 ppm, preferably from about 50 to about 1,000 ppm, and most preferably from about 200 to about 800 ppm, based on the total weight of liquid reaction medium.

The co-catalyst(s) is employed in amounts effective to increase the rate and/or selectivity of the hydroxylation reaction. Thus, while any effective amount of co-catalyst can be employed, it is contemplated that such effective amounts constitute typically from about 0.5 to about 100,000 ppm., preferably from about 25 to about 2,000 ppm., and most preferably from about 100 to about 2,000 ppm., by weight based on the total weight of the liquid contents of the reaction vessel.

Alternatively, the amount of co-catalyst can be expressed as a molar ratio between the molar amount of carboxylate species in the co-catalyst to the molar amount of osmium metal in the osmium catalyst. Accordingly, such molar ratios typically will vary from about 0.1:1 to about 500:1, preferably from about 1:1 to about 50:1, and most preferably from about 2:1 to about 10:1.

The oxidant which is employed to oxidize the olefin is at least one organic hydroperoxide.

Conventional organohydroperoxides include those having the formula:

$$R''OOH \qquad (II)$$

wherein R" is a substituted or unsubstituted: alkyl, typically about $C_3$ to about $C_{20}$, preferably about $C_3$ to about $C_{10}$, most preferably about $C_3$ to about $C_6$ alkyl; aryl, typically $C_6$ to $C_{14}$, preferably $C_6$ to $C_{10}$, most preferably $C_6$ aryl; aralkyl and alkaryl wherein the aryl and alkyl groups thereof are as defined immediately above; cycloalkyl, typically about $C_4$ to about $C_{20}$, preferably about $C_4$ to about $C_{10}$, most preferably about $C_4$ to about $C_8$ cycloalkyl; as well as oxacyclic having 1 to about 5 oxygens and preferably 3 to about 20 carbons, and azacyclic having 1 to about 5 nitrogens and preferably about 3 to about 20 carbons; and wherein the substituents of said R" group include halogen, hydroxyl, ester and ether groups.

Representative examples of suitable organohydroperoxides include ethylbenzyl hydroperoxide, t-butyl hydroperoxide, t-amyl hydroperoxide, cumene hydroperoxide, 2-methyl-2-hydroperoxy-methyl propionate, 2-methyl-2-hydroperoxy propanoic acid, pyrrolehydroperoxide, furan hydroperoxide, 2-butylhydroperoxide, cyclohexyl hydroperoxide, and 1-phenylethylhydroperoxide.

The most preferred organic hydroperoxides include t-butyl hydroperoxide, ethylbenzyl hydroperoxide, and t-amyl hydroperoxide. Frequently these hydroperoxides are made by the molecular oxygen oxidation of the corresponding hydrocarbon which also produces an alcohol as a by-product. For example, when isobutane is oxidized with molecular oxygen there is produced tertiary butyl hydroperoxide and tertiary butyl alcohol. It is preferred to avoid separation of the alcohol from the hydroperoxide since the alcohol can function as a diluent or solvent.

The amount of organohydroperoxide employed is not critical and can vary widely. Generally, the organohydroperoxide is employed in less than stoichiometric requirements (i.e., less than 1:1 molar ratio of organohydroperoxide per mole of ethylenic unsaturation in the olefin to be hydroxylated. Thus, while any amount of hydroperoxide effective to hydroxylate the olefin can be employed, it is contemplated that such effective amounts constitute a ratio of moles of ethylenic unsaturation in the olefin to be hydroxylated to moles of organohydroperoxide of from about 0.5:1 to about 100:1, preferably from about 1:1 to about 20:1 and most preferably from about 2:1 to about 10:1.

While the organohydroperoxide can be added to the reaction mixture in anhydrous form, it is preferred to add the organohydroperoxide as an aqueous solution comprising from about 1 to about 99%, preferably from about 10 to about 90%, and most preferably from about 20 to about 70%, by weight hydroperoxide, based on the weight of the aqueous hydroperoxide solution.

It is also critical to have water present during the hydroxylation reaction since the water is believed to contribute at least one of the oxygen molecules constituting one of the hydroxyl groups in the resulting glycol. The source of this water is not critical. Water can thus be added separately, and/or preferably as the solvent for the organohydroperoxide. Consequently, water is provided to, and/or is present in, the initial reaction mixture in at least a stoichiometric molar ratio with the molar amount of ethylenic unsaturation of the olefin to be hydroxylated. Such ratios preferably also are present in the reaction mixture at any given time after start-up. Accordingly, water is present in the reaction mixture at molar ratios of water to olefin ethylenic unsaturation to be hydroxylated in the reaction mixture of from about 1:1 to about 100:1, preferably from about 1:1 to about 50:1, and most preferably from about 1:1 to about 20:1. Such molar ratios typically can be achieved by controlling the amount of water in the reaction mixture to be from about 1 to about 90 percent, preferably from about 15 to about 85 percent, and most preferably from about 20 to about 60 percent, by weight, based on the total weight of the reaction mixture. Preferably the amount of water employed is less than that which will cause separation of the reaction mixture into an aqueous phase and organic phase although this is not a critical condition.

Olefins which can be hydroxylated in accordance with the present invention contain at least one ethylenic unsaturation and comprise any of the unsaturated aliphatic or alicyclic compounds well known in the art for undergoing such hydroxylation reactions with the proviso that the olefin is not also a carboxylic acid or salt thereof. Typically, such compounds will contain from about 2 to about 20 carbons, preferably from about 2 to about 10 carbons, and most preferably from about 2 to about 5 carbons. Such compounds may be straight or branched chain, mono-olefinic, di-olefinic, or poly-olefinic, conjugated or non-conjugated. They may be substituted with such groups as aryl, preferably aryl of from 6 to about 14 carbons, alkyl, preferably alkyl of from 1 to 10 carbons, or aralkyl and alkaryl wherein the alkyl and aryl portions thereof are as described above, as well as with functional groups such as hydroxyl.

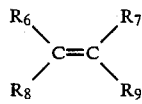
(III)

wherein $R_6$, $R_7$, $R_8$, and $R_9$, which may be the same or different, are selected from the group consisting of hydrogen; substituted or unsubstituted: alkenyl, aralkenyl, alkyl, aryl, alkaryl, and aralkyl hydrocarbyl groups, said hydrocarbyl groups being preferably as defined immediately above; or any two of said $R_{6-9}$ groups together can constitute a cycloalkyl group typically of from about 4 to about 12, preferably from about 5 to about 8 carbons.

Representative olefins which can be hydroxylated and contain at least one ethylenic unsaturation include: ethylene, propylene, butene-1, butene-2, isobutene, butadiene, pentene-1, pentene-2, hexene, isohexene, heptane, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, octylcyclohexene, dodecyclohexene, acrolein, methyl methacrylate, styrene, and mixtures thereof.

The preferred olefins are ethylene, propylene, isobutylene, butadiene, styrene, allyl alcohol and allyl chloride.

The most preferred olefins are ethylene and propylene.

The preferred mode for conducting the hydroxylation reaction is to contact the osmium catalyst with a liquid reaction mixture, preferably provided as a homogeneous or substantially homogeneous medium and preferably, by optionally, by using an inert organic solvent to dissolve or assist in dissolving the osmium catalyst, cocatalyst and reactants.

Partial immiscibility of the solvent with water is acceptable although not preferred. By an inert solvent is meant one which does not undergo oxidation during the course of the reaction.

Suitable inert organic solvents preferably possess polar functional groups and include aliphatic or aromatic alcohols having from 1 to about 10 carbon atoms, preferably tertiary alcohols, aliphatic or aromatic ketones having from 3 to about 10 atoms, aliphatic or alicyclic ethers having from 2 to about 10 carbon atoms, glycols having from 2 to about 10 carbon atoms, N,N-dialkyl amides having from 3 to about 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, ethylbenzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide dimethyl sulfone, diethyl sulfone, tetra methylene sulfone, diphenyl sulfone, acetonitrile, pyridine, dioxane, tetra hydrofuran, tetra hydropyran, dioxolane, and mixtures thereof.

The preferred solvents include those which are substantially or completely miscible with water such as t-butyl alcohol, methanol, and acetonitrile.

The most preferred solvent(s) is the hydroxylated olefin which possesses at least one glycol functionality or mixtures of the product glycol and the product alcohol derived from the organohydroperoxide.

For example, when ethylene is hydroxylated using t-butyl hydroperoxide, the preferred solvent is ethylene glycol, t-butyl alcohol, or a mixture of ethylene glycol and t-butyl alcohol, the latter being formed in-situ from t-butyl hydroperoxide. The former (product glycol) avoids solvent separation process steps and the latter is economical since the ethylene glycol and t-butyl alcohol are both saleable products which have to be separated anyway. In either instance, an additional solvent separation step is avoided.

The inert solvent is preferably employed in amounts sufficient to achieve a homogeneous solution with respect to at least the olefin and oxidant. Typically such amounts can vary from about 0 to about 90 percent, preferably from about 20 to about 80 percent, and most preferably from about 20 to about 50 percent, by weight, based on the total weight of the reaction mixture.

While the above description with respect to the identity and use of the inert solvent applies when employing carboxylate salt co-catalysts wherein the cation is any of alkali metals, alkaline earth metals, and transition metals, the same is not true when the cation of the carboxylate salt co-catalyst is any of tetra hydrocarbyl ammonium or phosphonium. In the latter instance, the solvent which is employed in accordance with the process of the present invention must comprise at least 50%, preferably at least 70%, and most preferably at least 90% (e.g. 100%) of the product glycol (e.g., ethylene glycol or propylene glycol) and/or the organic hydroperoxide derived by-product alcohol as described above. The by-product alcohols of t-butyl hydroperoxide, ethylbenzyl hydroperoxide, and t-amyl hydroperoxide are t-butyl alcohol, ethylbenzyl alcohol, t-amylalcohol respectively. The organic solvent preferably will exclude acetone.

The pH of the reaction mixture during the hydroxylation reaction need not be rigidly controlled although it will typically not be allowed to drop below about 4, preferably not below about 6. Likewise, the pH of the reaction mixture typically will not be allowed to exceed about 12 although the process can still be conducted at a pH below 4 and above 12. Accordingly, the pH of the reaction mixture typically will be maintained between 4 and 12, preferably between about 6 and about 12, and most preferably between about 7 and about 12. The pH of the reaction mixture can be controlled by the use of conventional buffers or base where needed. Preferably, pH control is achieved by the use of base.

In carrying out a preferred embodiment of the invention, olefin, water, oxidant, osmium containing catalyst, co-catalyst, and optional inert solvent are contacted, e.g., by admixing to form a liquid reaction medium in a manner and under conditions sufficient to hydroxylate the olefin, i.e., to convert at least one of the ethylenic unsaturations possessed thereby to its corresponding vicinal diol. The manner and order of addition of each of the individual components of the liquid reaction medium to the reaction vessel is not critical. However, it is preferred to mix the osmium containing catalyst, and co-catalyst with an aqueous solution of the hydroperoxide and then add solvent, additional additives such as buffers, where needed, and finally olefin.

Accordingly, the initial typical reaction medium prior to introduction of olefin will typically comprise: (a) an organohydroperoxide in an amount of from about 1 to 70 percent, preferably from about 5 to about 60 percent, and most preferably from about 10 to about 50 percent, by weight, based on the weight of the reaction medium exclusive of the weight of olefin, catalyst, and any other additive if present; (b) osmium containing catalyst in amounts heretofore specified; (c) water subject, to the molar constraints heretofore specified, in an amount of from about 1 to about 98 percent, preferably from about 10 to about 80 percent, and most preferably from about 30 to about 60 percent, by weight, based on the total weight of the reaction medium exclusive of the weight of olefin, catalyst, and any other additives if present; and (d) inert organic solvent in an amount of from about 0 to about 99 percent, preferably from about 20 to about 80 percent, and most preferably from about 30 to about 60 percent, by weight, based on the weight of the reaction medium exclusive of the weight of olefin, catalyst, and other additives if present. Co-catalyst is used in effective amounts as described above as are buffers to control pH where desired.

For the production of ethylene glycol, propylene glycol or any product derived from any unsaturated gaseous olefin, the latter may be bubbled through the reaction mixture containing the components described herein or it may be introduced under pressure. However, it is preferred that the reaction takes place in the liquid phase. Consequently, sufficient pressure is preferably employed to maintain the gaseous reactants in the liquid phase. Otherwise, the reaction pressure is not critical and can be atmospheric, sub-atmospheric, or super-atmospheric.

When the olefin reactant is a liquid or is dissolved in the reaction mixture under pressure, its concentration in the reaction mixture typically will vary from about 1 to about 98 percent, preferably from about 10 to about 80 percent, and most preferably from about 30 to about 60 percent, by weight, based on the total weight of the reactant mixture inclusive of the weight of components (a) through (d) described above.

The hydroxylation reaction is typically conducted at temperatures which can vary over wide limits although it is preferred to maintain the reaction mixture in the liquid phase. Accordingly, typical reaction temperatures can vary from about 0° to about 250° C., preferably from about 20° to about 150° C., and most preferably from about 30° to about 130° C.

At temperatures greater than the aforenoted ranges, the reaction rate may increase substantially but this usually occurs at the expense of a significant reduction in selectivity. At very low reaction temperatures, e.g. below about 0° C. the reaction rate decreases to a commercially undesirable degree. Accordingly, while the reaction temperature is not critical and can vary over a wide range, one normally would not operate at temperature extremes outside the aforenoted ranges.

The hydroxylation reaction can be performed as a batch reaction, as a continuous reaction or as a semicontinuous reaction.

In the batch reaction, a reaction medium containing the above described components is charged into the reaction vessel along with olefin if in liquid form. Alternatively, the reaction vessel is then pressurized with olefin if in gaseous form. It may be desirable to heat the liquid reaction mixture to reaction temperature prior to pressurizing with the reactant gases. The reaction is allowed to proceed to completion, typically for a period of from about 0.5 to about 5 hours, preferably from about 0.5 to 3 hours, and most preferably from about 0.5 to about 2 hours.

In the continuous process, the components can be introduced into the inlet of an elongated reactor at a rate such that substantially complete reaction will have taken place by the time the reaction mixture reaches the reactor outlet. The reaction can be carried out in a semi-continuous manner by metering the reactant mixture components into a series of two or more tank reactors at the appropriate rate to maintain the reactor liquid level.

Additionally, the process may be run in either of the aforementioned modes by altering the reaction conditions, and/or, the reactant, solvent, catalyst, cocatalyst, and pH control additive concentrations during the course of the reaction. Thus, the process may be run by changing the temperature, pressure, catalyst concentration, oxidant concentration, and/or olefin concentration.

The spent reaction mixture after removal of unreacted olefin is a solution of product glycol, by-products if any, solvent, water, catalyst and co-catalyst. The volatile components are distilled out of the reaction mixture into various fractions leaving non-volatile catalyst components in the still. The product glycol is then separated from the high boiling distillate and preferably a portion of it and/or the organic hydroperoxide derived by-product alcohol is recycled to the reaction zone to serve as a solvent.

The following examples are given as specific illustrations of the claimed invention. It should be understood, however, that the invention is not limited to the specific details set forth in the examples. All parts and percentages in the examples as well as in the remainder of the specification are by weight unless otherwise specified. Furthermore and unless otherwise specified, while the following examples are written in the present tense, they represent work actually performed.

Unless otherwise specified, in the following examples selectivity, conversion and yield are calculated as follows:

$$\% \text{ selectivity} = \frac{\text{moles of glycol formed}}{\text{moles of hydroperoxide consumed}} \times 100$$

$$\% \text{ conversion} = \frac{\text{moles of hydroperoxide reacted}}{\text{moles of hydroperoxide charged}} \times 100$$

$$\% \text{ yield} = \% \text{ conversion} \times \% \text{ selectivity}$$

EXAMPLE 1

Into a 100 ml round-bottom flask provided with a condenser, addition funnel, magnetic stirrer and thermometer is charged 4 ml of a 0.4 weight % solution of $OsO_4$ in $H_2O$, 5.0 g of 1-octene, 0.125 mmole of sodium acetate (i.e. NaOAc), and 20.0 g of t-butanol. The mixture is stirred and 3.0 g of a 70 weight % solution of t-butyl hydroperoxide (23 mmole) in water is added thereto slowly over 30 minutes. The temperature range during the addition is 27°–45° C. The NaOAc to $OsO_4$ molar ratio is therefore 2:1. The solution is analyzed by gas chromatography (GC). Complete conversion of the tertiary butyl hydroperoxide is obtained with selectivity to 1,2-octanediol of 66%.

EXAMPLE 2

Example 1 is repeated, with the exception that tetraethyl ammonium acetate (i.e. $Et_4NOAc$) replaces NaOAc. The molar ratio of $Et_4NOAc$) to $OsO_4$ is 2:1. Complete conversion of the hydroperoxide is obtained and selectivity to the glycol is 55%.

EXAMPLE 3

Example 1 is repeated with the exception that $Et_4NOAc$ is the co-catalyst and the molar ratio of $Et_4NOAc$ to $OsO_4$ is 125:1. Complete conversion of the hydroperoxide is obtained with selectivity to the glycol is about 86%.

EXAMPLE 4

Example 1 is repeated with the exception that $Cu(OAc)_2$ is employed as the co-catalyst and the molar ratio of $Cu(OAc)_2$ to $OsO_4$ is 2:1. Complete conversion of the hydroperoxide is obtained and selectivity to the glycol is 34%.

COMPARATIVE EXAMPLE 1

Example 3 is repeated with the exception that acetone (20.0 g) is employed as the solvent instead of t-butanol, the mole ratio of $Et_4NOAc$ to $OsO_4$ remaining at 125:1. Complete conversion of the hydroperoxide is obtained and the selectivity to 1,2-octane diol is 88%.

COMPARATIVE EXAMPLE 2

This example illustrates the effect of omitting a co-catalyst from the reaction mixture.

Example 1 is repeated with the exception that no NaOAc is used as co-catalyst. Complete conversion of the t-butyl hydroperoxide is obtained and selectivity to the glycol is 19%.

COMPARATIVE EXAMPLE 3

Example 1 is repeated with the exception that $(Et)_4N\ NO_3$ is used as co-catalyst in place of NaOAc. Thus, $(Et)_4N$ (0.12 mmol) is charged along with $OsO_4$. Complete conversion of the hydroperoxide is obtained and selectivity to the glycol is 22%.

DISCUSSION OF RESULTS

Comparing Examples 1 and 2 it can be seen that at low molar ratios of co-catalyst to $OsO_4$, sodium acetate performs better than tetra ethyl ammonium acetate. This is also significant from an economic standpoint in that sodium acetate is much cheaper than tetra ethyl ammonium acetate.

Comparing Example 3 with Comparative Example 1 it can be seen that the use of t-butyl alcohol, instead of acetone as per Sharpless et al, results in only a slight 2% drop in selectivity. However, the use of t-butyl alcohol results in a substantial simplification of the process and a substantial improvement in process economics.

Comparative Example 2 illustrates the effect of omitting the co-catalyst, namely, selectivity to glycol drops from 66% to 19%.

Example 4 illustrates the effect of employing a transition metal as the cation of the carboxylate salt, i.e., a selectivity to glycol of 34%.

Comparative Example 3 illustrates the criticality of the carboxylate anion as the source of the co-catalytic effect by substituting tetraethyl ammonium nitrate for tetraethyl ammonium acetate namely, the glycol selectivity is reduced from 55% (Example 2) to 22%.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for hydroxylating olefins which comprises reacting at least one olefinic compound having at least one ethylenic unsaturation and which is not a carboxylic acid or salt thereof, with at least one organic hydroperoxide and water in the presence of a catalyst composition under conditions and in a manner sufficient to convert at least one of said ethylenic unsaturation to its corresponding vicinal diol, said catalyst composition comprising:

(a) at least one unsupported osmium oxide capable of catalyzing said hydroxylation reaction; and (b) as a co-catalyst at least one organic carboxylate salt having a cation and an anion, said cation being selected from the group consisting of tetrahydrocarbyl phosphonium and cations of Fe, Co, Ni, Cu, and Mn; said co-catalyst being capable of increasing at least one of the rate and selectivity of the hydroxylation reaction to product diol relative to the rate and selectivity in the absence of said co-catalyst.

2. The process of claim 1 wherein the osmium oxide is OsO$_4$.

3. The process of claim 1 wherein the anion of the carboxylate salt is represented by the structural formula:

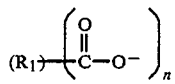

wherein R$_1$ represents a substituted or unsubstituted hydrocarbyl group selected from the group consisting of saturated aliphatic, saturated alicyclic, aromatic, and mixtures thereof and n is a number of from 1 to about 10.

4. The process of claim 3 wherein the R$_1$ hydrocarbyl group is selected from the group consisting of saturated aliphatic having from about 1 to about 10 carbons exclusive of substituents, saturated alicyclic having from about 4 to about 12 carbons exclusive of substituents, and aromatic having from about 6 to about 14 carbons exclusive of substituents; n is a number from 1 to 5; and said substituents are selected from the group consisting of: alkyl of from about 1 to about 10 carbons; aryl of from about 6 to about 14 carbons; hydroxy; ether groups represented by the structural formula selected from —O—R$_2$ and —R$_3$—O—R$_2$ wherein R$_2$ and R$_3$ are independently selected from alkyl of from about 1 to about 10 carbons; and ester groups represented by the strucutral formula selected from the group consisting of

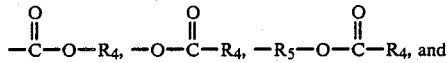

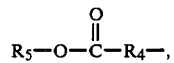

wherein R$_4$ and R$_5$ which may the same or different are as defined in connection with R$_2$ and R$_3$.

5. The process of claim 3 wherein the R$_1$ hydrocarbyl group is unsubstituted and n is 1.

6. The process of any one of claims 1 and 2 wherein the carboxylate salt is selected from the group consisting of copper acetate, copper benzoate, iron acetate, iron benzoate, and mixtures thereof.

7. The process of claim 1 wherein the olefinic compound is selected from the group consisting of ethylene, propylene, and mixtures thereof.

8. The process of claim 1 wherein the hydroxylation reaction is conducted in the liquid phase and in the presence of at least one inert organic solvent.

9. The process of claim 8 wherein the organic solvent comprises at least about 70%, by solvent weight, of said hydroxylated product, by-product alcohol, and mixture thereof.

10. The process of claim 1 wherein water is initially present in said reaction mixture in at least a stoichiometric molar ratio with the molar amount of said ethylenic unsaturation to be hydroxylated.

* * * * *